(12) United States Patent
Hao et al.

(10) Patent No.: US 11,116,707 B2
(45) Date of Patent: *Sep. 14, 2021

(54) METHODS FOR SYNTHESIZING STANNOUS PYROPHOSPHATE

(71) Applicant: Colgate-Palmolive Company, New York, NY (US)

(72) Inventors: Zhigang Hao, Bridgewater, NJ (US); Long Pan, Somerset, NJ (US); Yu Wang, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/830,559

(22) Filed: Mar. 26, 2020

(65) Prior Publication Data
US 2020/0330343 A1 Oct. 22, 2020

Related U.S. Application Data

(60) Provisional application No. 62/835,768, filed on Apr. 18, 2019.

(51) Int. Cl.
*A61K 8/24* (2006.01)
*A61Q 11/00* (2006.01)

(52) U.S. Cl.
CPC .............. *A61K 8/24* (2013.01); *A61Q 11/00* (2013.01); *A61K 2800/84* (2013.01)

(58) Field of Classification Search
None
See application file for complete search history.

(56) References Cited

U.S. PATENT DOCUMENTS

| 3,028,216 A | 4/1962 | Gemmell et al. |
| 2017/0231878 A1 | 8/2017 | Schankel et al. |
| 2018/0168956 A1 | 6/2018 | Rege et al. |
| 2018/0168957 A1 | 6/2018 | Rege et al. |

FOREIGN PATENT DOCUMENTS

| CN | 101234757 | 8/2008 |
| CN | 104958208 | 10/2015 |

OTHER PUBLICATIONS

CN104958208A, Jiangsu Qilikang Skin Pharmaceutical Co. Ltd, "Toothpaste for helping digestion and promoting appetite and preparation method thereof," Oct. 7, 2015, English language machine translation of abstract, Espacenet, date obtained: Aug. 19, 2020, 1 page <https://worldwide.espacenet.com/patent/search/family/054212427/publication/CN104958208A?q=CN104958208>.
CN101234757A, Hexiang Yi, "Method for preparing stannous pyrophosphate," Aug. 6, 2008, English machine language translation of abstract, Espacenet, date obtained: Aug. 19, 2020, 1 page <https://worldwide.espacenet.com/patent/search/family/039918700/publication/CN101234757A?q=CN101234757A>.

*Primary Examiner* — Brian J Davis

(57) ABSTRACT

Disclosed herein are improved methods for the synthesis of stannous pyrophosphate, as well as improved methods for the manufacture of oral care compositions comprising stannous pyrophosphate.

20 Claims, 4 Drawing Sheets

METHODS FOR SYNTHESIZING STANNOUS PYROPHOSPHATE

CROSS-REFERENCE TO RELATED APPLICATIONS

This application is a United States application filed under 35 U.S.C. § 111(a) claiming priority to and the benefit of U.S. Provisional Application No. 62/835,768, filed on Apr. 18, 2019, the contents of which are hereby incorporated by reference in its entirety.

BACKGROUND

Oral cavity bacteria are the primary cause of dental ailments, including caries, gingivitis, periodontitis, and halitosis. Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis and in the treatment or prevention of erosive tooth demineralization. Stannous fluoride is well known for use in clinical dentistry with a history of therapeutic benefits over forty years. However, until recently, its popularity has been limited by its instability in aqueous solutions. The instability of stannous fluoride in water is primarily due to the reactivity of the stannous ion ($Sn^{2+}$). Stannous salts readily hydrolyze at a pH above 4, resulting in precipitation from solution. It has traditionally been thought that this formation of insoluble stannous salts results in a loss of therapeutic properties.

Soluble metal ions, such as stannous, may also react unfavorably polymeric rheological modifiers, such as modified celluloses (e.g., carboxymethyl cellulose) and gums (e.g., xanthan gum or carrageenan gum). Such compounds often considered to be incompatible with divalent metal ions.

Recently there has been a renewed interest in using insoluble stannous salts in oral care compositions as a way of overcoming these issues. One leading contender is stannous pyrophosphate, an agent which has been known since at least the 1960's as a dentifrice polishing agent. Stannous pyrophosphate (also known as SnPP) has the formula $Sn_2P_2O_7$, and it combines the tetravalent pyrophosphate anion with divalent Sn(II) cation. It is substantially insoluble in water, especially at an acidic pH.

The use of stannous pyrophosphate in making oral care products has been limited by its high cost. Stannous pyrophosphate is significantly more expensive to purchase on the global chemical market than other more common stannous compounds, such as stannous chloride and stannous fluoride. Therefore, oral care products can be manufactured much more cost effectively if a low-cost stannous salt, such as stannous chloride, is purchased as a material from which stannous pyrophosphate can be made.

Various methods of synthesizing stannous pyrophosphate have been known in the art. For example, Gemmell et al. synthesize SnPP by reacting an aqueous slurry or solution of stannous chloride with sodium acid pyrophosphate (disodium pyrophosphate) followed by neutralization with excess base (such as sodium hydroxide or sodium carbonate). See U.S. Pat. No. 3,028,216. One drawback of this is that the reaction results in a sodium chloride by-product which can be difficult to remove, hindering the production of highly pure stannous pyrophosphate. In some cases, this impurity can impart a highly undesirable salty taste to the product. This is especially true if this prior art method is adapted as an in-situ method of making stannous pyrophosphate during the manufacture of the oral care product itself.

There is thus still a need for additional methods which provide improved ease, efficiency and/or yield.

BRIEF SUMMARY

It has now been discovered that stannous pyrophosphate (SnPP) can be more efficiently prepared by reacting stannous chloride with a tetrapotassium pyrophosphate (TKPP), dipotassium pyrophosphate (DKPP), or disodium pyrophosphate (DSPP), in a water or water/alcohol mixture, followed by precipitation, filtration and freeze-drying, to obtain highly pure product without by-products causing off-flavors. In addition, it has been further discovered that an oral care composition comprising stannous pyrophosphate can be more effectively prepared by reacting stannous chloride with tetrapotassium pyrophosphate, dipotassium pyrophosphate or disodium pyrophosphate in a water or water/alcohol mixture, optionally followed by precipitation, filtration and resuspension, at the point of manufacture of the oral care composition. The latter "in-situ" method provides improved economies of manufacture by reducing costs associated with transport, storage, and purification of the stannous pyrophosphate material made from the stannous chloride.

The prior art use of stannous chloride and tetrasodium pyrophosphate to make stannous pyrophosphate results in the formation of sodium chloride as a by-product. The stoichiometry of the reaction results in the formation of a 4:1 molar ratio of sodium chloride to stannous pyrophosphate in the product: $2SnCl_2 + Na_4P_2O_7 \rightarrow 4NaCl + Sn_2PO_7$. This would be expected to impart a salty taste to the product which could be adverse in some markets. The present disclosure helps overcome this problem by using either (1) disodium pyrophosphate or (2) a potassium pyrophosphate salt as the starting material for the reaction. By using disodium pyrophosphate instead of tetrasodium pyrophosphate, the molar quantity of sodium chloride by-product is reduced by half: $2SnCl_2 + Na_2H_2P_2O_7 \rightarrow 2NaCl + 2HCl + Sn_2PO_7$. By using dipotassium or tetrapotassium pyrophosphate instead of the corresponding sodium pyrophosphate, the resulting by-product is potassium chloride instead of sodium chloride. Potassium chloride is known to have a much less-salty taste than sodium chloride. In addition, without being bound by theory, the presence of potassium chloride in the resulting oral care composition may provide an anti-sensitivity benefit as well (soluble potassium salts inhibit nerve firing in dental pulp nerves).

The invention further provides oral care compositions, for example mouthwash, oral gel or dentifrice compositions, that comprise the stannous pyrophosphate made according to the present synthetic methods.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
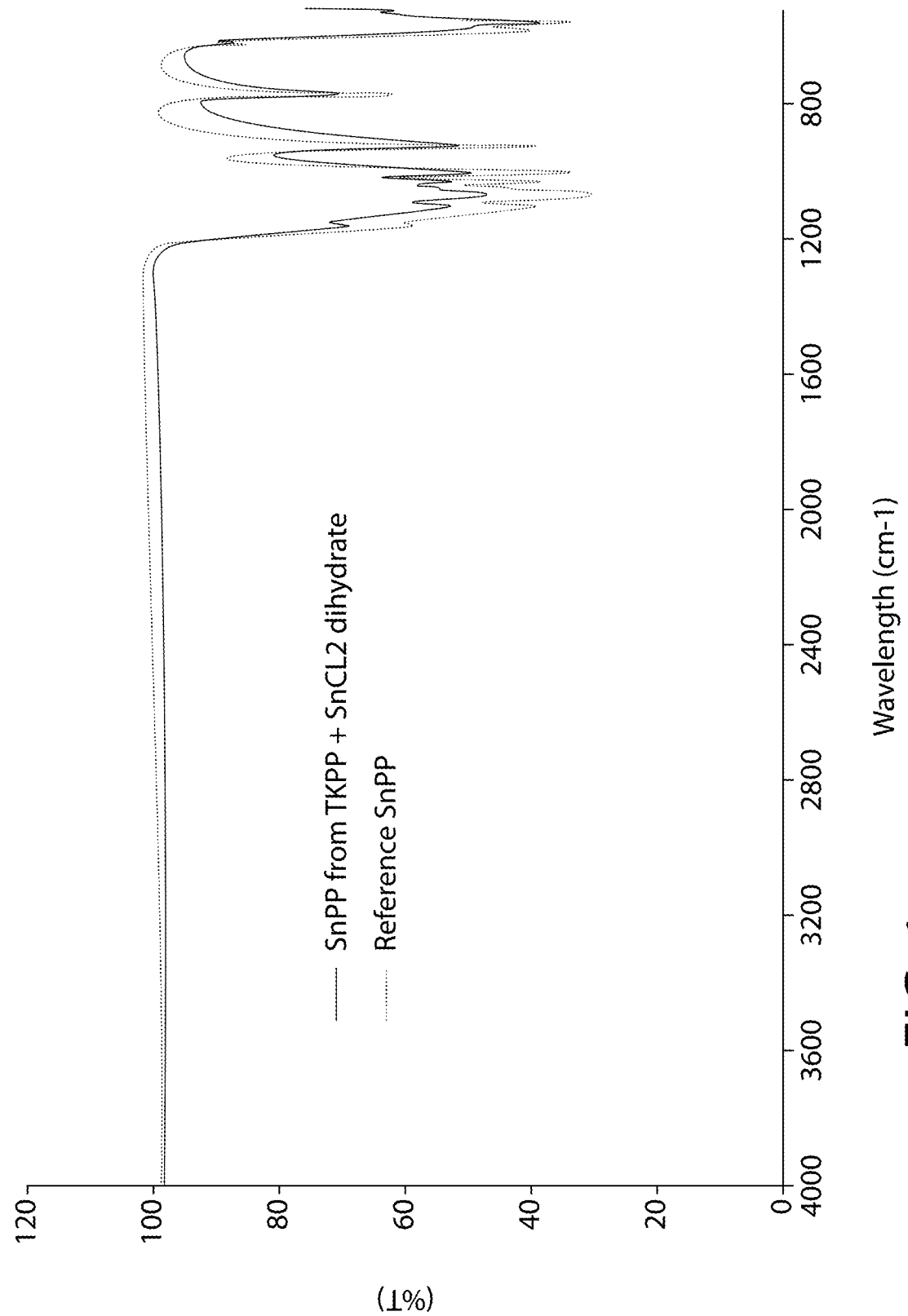
FIG. 1 shows overlaid Fourier-transform infrared (FTIR) spectra comparing the SnPP product made according to the present disclosure, by reacting stannous chloride and tetrapotassium pyrophosphate (TKPP) in water for 30 minutes, followed by precipitation, filtration and freeze-drying (spectrum in grey) compared to reference SnPP purchased from a global chemical supplier (spectrum in black).

The following description of the preferred embodiment(s) is merely exemplary in nature and is in no way intended to limit the invention, its application, or uses.

The invention therefore provides, in a first aspect, a method of making stannous pyrophosphate (Method 1), comprising the steps of (1) reacting stannous chloride with tetrapotassium, dipotassium or disodium pyrophosphate in a water or water/alcohol solvent mixture, (2) precipitating the stannous pyrophosphate product, (3) recovering the stannous pyrophosphate product by filtration, and (4) freeze-drying the stannous pyrophosphate product. In further embodiments of Method 1, the present disclosure provides:

1.1. Method 1 wherein the stannous chloride is stannous chloride dihydrate ($SnCl_2 \cdot 2H_2O$).
1.2. Method 1 or 1.1, wherein the pyrophosphate is dipotassium pyrophosphate or tetrapotassium pyrophosphate.
1.3. Method 1 or any of 1.1 et seq., wherein the stannous chloride and the pyrophosphate are combined in a molar ratio of 1:1 to 1:3, e.g., from 1:1 to 1:2 or from 1:1 to 1.5, or from 1:1 to 1.25, or about 1:1.
1.4. Method 1 or any of 1.1 et seq., wherein solvent for step (1) is water.
1.5. Method 1 or any of 1.1 et seq., wherein the solvent for step (1) is a water/alcohol mixture.
1.6. Method 1.5, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.
1.7. Method 1.6, wherein the alcohol is selected from 1,2-propylene glycol, 1,3-propylene glycol, glycerol and sorbitol.
1.8. Method 1.5, 1.6 or 1.7, wherein the ratio of water to alcohol is 5:1 to 1:5 v/v, e.g., 4:1 to 1:4, 3:1 to 1:3, or 2:1 to 1:2.
1.9. Method 1 or any of 1.1 et seq., wherein step (1) takes place at 20° C. to 100° C., e.g., at 25° C. to 80° C., or at 35° C. to 70° C., or at 45° C. to 70° C., or at 55° C. to 70° C., or at about 65° C.
1.10. Method 1 or any of 1.1 et seq., wherein step (1) takes place at 20° C. to 35° C. or at 20° C. to 30° C.
1.11. Method 1 or any of 1.1 et seq., wherein the reaction mixture is allowed to cool between step (1) and step (2), e.g., to cool to room temperature (e.g., 20° C. to 30° C.
1.12. Method 1 or any of 1.1 et seq., wherein the precipitation of step (2) occurs unassisted, e.g., upon cooling of the reaction mixture from its reaction temperature.
1.13. Method 1 or any of 1.1 et seq., wherein the precipitation of step (2) is promoted by the addition of water to the reaction mixture of step (1), e.g., cold water (e.g., water at a temperature of 0° C. to 25° C.).
1.14. Method 1 or any of 1.1 et seq., wherein the filtered product from step (3) is washed one or more times with water before step (4).
1.15. Method 1.14, wherein the filtered product from step (3) is washed once, twice or three times with water before step (4).
1.16. Method 1 or any of 1.1 et seq., wherein the reaction step (1) is substantially complete (e.g., greater than 90% conversion) in 0-3 hours, e.g., in 0-2 hours or in 0-1 hour, or in 0-30 minutes, e.g., in 1-30 minutes, or 1-20 minutes, or 1-15 minutes or 1-10 minutes.
1.17. Method 1 or any of 1.1 et seq., wherein the method does not comprise the use or addition of any reactants, reagents or other chemicals other than the stannous chloride, the pyrophosphate salt (e.g., the tetrapotassium, dipotassium or disodium pyrophosphate), the water or water/alcohol solvent mixture, and optionally the washing water (e.g., the method does not comprise the addition of any base).
1.18. Method 1 or any of 1.1 et seq., wherein the method further comprises the step of isolating the stannous pyrophosphate product, and/or the step of packaging the stannous pyrophosphate product.
1.19. Stannous pyrophosphate made according to Method 1 or any of Methods 1.1 to 1.18.
1.20. An oral care composition comprising stannous pyrophosphate made according to Method 1 or any of 1.1 to 1.18.

In another aspect, the invention further provides a method of making an oral care composition comprising stannous pyrophosphate (Method 2), comprising the steps of (1) reacting stannous chloride with tetrapotassium, dipotassium or disodium pyrophosphate in a water or water/alcohol solvent mixture in a reactor tank, (2) precipitating the stannous pyrophosphate product, optionally (3) recovering the stannous pyrophosphate product by filtration, optionally (4) freeze-drying the stannous pyrophosphate product, and (5) transferring the stannous pyrophosphate product into a mixing tank containing at least one oral care ingredient and at least one orally acceptable solvent.

In further embodiments of Method 2, the present disclosure provides:

2.1. Method 2 wherein the stannous chloride is stannous chloride dihydrate ($SnCl_2 \cdot 2H_2O$).
2.2. Method 2 or 2.1, wherein the pyrophosphate is dipotassium pyrophosphate or tetrapotassium pyrophosphate.
2.3. Method 2 or any of 2.1 et seq., wherein the stannous chloride and the pyrophosphate are combined in a molar ratio of 1:1 to 1:3, e.g., from 1:1 to 1:2 or from 1:1 to 1.5, or from 1:1 to 1.25, or about 1:1.
2.4. Method 2 or any of 2.1 et seq., wherein solvent for step (1) is water.
2.5. Method 2 or any of 2.1 et seq., wherein the solvent for step (1) is a water/alcohol mixture.
2.6. Method 2.5, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.
2.7. Method 2.6, wherein the alcohol is selected from 1,2-propylene glycol, 1,3-propylene glycol, glycerol and sorbitol.
2.8. Method 2.5, 2.6 or 2.7, wherein the ratio of water to alcohol is 5:1 to 1:5 v/v, e.g., 4:1 to 1:4, 3:1 to 1:3, or 2:1 to 1:2.
2.9. Method 2 or any of 2.1 et seq., wherein step (1) takes place at 20° C. to 100° C., e.g., at 25° C. to 80° C., or at 35° C. to 70° C., or at 45° C. to 70° C., or at 55° C. to 70° C., or at about 65° C.
2.10. Method 2 or any of 2.1 et seq., wherein step (1) takes place at 20° C. to 35° C. or at 20° C. to 30° C.
2.11. Method 2 or any of 2.1 et seq., wherein the reaction mixture is allowed to cool between step (1) and step (2), e.g., to cool to room temperature (e.g., 20° C. to 30° C.
2.12. Method 2 or any of 2.1 et seq., wherein the precipitation of step (2) occurs unassisted, e.g., upon cooling of the reaction mixture from its reaction temperature.
2.13. Method 2 or any of 2.1 et seq., wherein the precipitation of step (2) is promoted by the addition of water to the reaction mixture of step (1), e.g., cold water (e.g., water at a temperature of 0° C. to 25° C.).
2.14. Method 2 or any of 2.1 et seq., wherein the step (3) and step (4) are omitted, and step (2) yields a liquid slurry of the stannous pyrophosphate product precipitate in the water or water/alcohol solvent mixture and this slurry is transferred into the mixing tank of step (5).
2.15. Method 2 or any of 2.1 et seq., wherein step (4) is omitted, and the filtered solid from step (3) is transferred into the mixing tank of step (5).
2.16. Method 2.15, wherein the filtered product from step (3) is washed one or more times with water before being transferred into the mixing tank of step (5).
2.17. Method 2.16, wherein the filtered product from step (3) is washed once, twice or three times with water before being transferred into the mixing tank of step (5).
2.18. Method 2.15, 2.16, or 2.17, wherein the filtered solid from step (3), optionally after washing with water, is resuspended in an orally acceptable liquid and the resulting suspension is transferred into the mixing tank of step (5).
2.19. Method 2.18, wherein the orally acceptable liquid is selected from water, glycerol, propylene glycol, sorbitol or a mixture thereof.
2.20. Method 2 or any of 2.1 et seq., wherein the reaction step (1) is substantially complete (e.g., greater than 90% conversion) in 0-3 hours, e.g., in 0-2 hours or in 0-1 hour, or in 0-30 minutes, e.g., in 1-30 minutes, or 1-20 minutes, or 1-15 minutes or 1-10 minutes.
2.21. Method 2 or any of 2.1 et seq., wherein method steps (1)-(5) do not comprise the use or addition of any reactants, reagents or other chemicals other than the stannous chloride, the pyrophosphate salt (e.g., the disodium, dipotassium or tetrapotassium pyrophosphate), the water or water/alcohol solvent mixture, the optional washing water and the optional orally acceptable liquid for resuspension of the filtered precipitate (e.g., the method does not comprise the addition of any base).
2.22. Method 2 or any of 2.1 et seq., wherein the method further comprises the step of incorporating stannous fluoride into the oral care composition.
2.23. An oral care composition made according to Method 2 or any of 2.1 to 2.22

In a third aspect, the present disclosure provides an oral care composition (Composition 3) comprising (a) stannous pyrophosphate and sodium chloride in a molar ratio of about 2 parts sodium chloride to one part stannous pyrophosphate, (b) stannous pyrophosphate and potassium chloride in a molar ratio of about 2 parts potassium chloride to one part stannous pyrophosphate, or (c) stannous pyrophosphate and potassium chloride in a molar ratio of about 4 parts potassium chloride to one part stannous pyrophosphate. In further embodiments of this aspect, the present disclosure provides:

3.1 Composition 3, wherein the composition comprises from 0.1 to 3% by weight of stannous pyrophosphate, e.g., from 0.5 to 2% by weight, or about 1% by weight.
3.2 Composition 3 or 3.1, wherein the composition comprises potassium chloride and stannous pyrophosphate in a molar ratio of about 3:1 to about 4:1, e.g., about 3.5:1 to about 4:1.
3.3 Composition 3, 3.1 or 3.2, wherein the composition comprises 0.1 to 3% by weight of potassium chloride, e.g., from 0.2 to 1.3% by weight, or about 0.75% by weight.
3.4 Composition 3 or 3.1, wherein the composition comprises potassium chloride and stannous pyrophosphate in a molar ratio of about 1:1 to about 2:1, e.g., about 1.5:1 to about 2:1.
3.5 Composition 3, 3.1 or 3.2, wherein the composition comprises 0.05 to 1.5% by weight of potassium chloride, e.g., from 0.1 to 0.65% by weight, or about 0.38% by weight.
3.6 Composition 3 or 3.1, wherein the composition comprises sodium chloride and stannous pyrophosphate in a molar ratio of about 1:1 to about 2:1, e.g., about 1.5:1 to about 2:1.
3.7 Composition 3, 3.1 or 3.2, wherein the composition comprises 0.01 to 1% by weight of sodium chloride, e.g., from 0.05 to 0.5% by weight, or about 0.3% by weight.
3.8 Composition 3 or any of 3.1 et seq., wherein the composition further comprises stannous fluoride, e.g., in an amount of 0.1 to 1.0 wt %, or about 0.45 wt %.
3.9 Composition 3 or any of 3.1 et seq., wherein the composition further comprises zinc citrate, zinc oxide or a combination thereof.

3.10 Composition 3.9, wherein the composition comprises from 0.1 to 1.0% by weight of zinc citrate (e.g., zinc citrate trihydrate), from 0.5 to 2.0% by weight of zinc oxide, or a combination thereof 3.11 Composition 3.10, wherein the composition comprises about 0.5% by weight of zinc citrate (e.g., zinc citrate trihydrate), about 1.0% zinc oxide, or a combination thereof.

3.12 Composition 3 or any of 3.1 et seq., wherein the composition further comprises one or more humectants, e.g., selected from glycerol, sorbitol, propylene glycol, and xylitol.

3.13 Composition 3 or any of 3.1 et seq., wherein the composition further comprises one or more abrasives (e.g., silica), anionic surfactants (e.g., sodium lauryl sulfate), zwitterionic surfactants (e.g., cocamidopropyl betaine), gums or polymers (e.g., methyl vinyl ether/maleic anhydride copolymer, sodium carboxymethyl cellulose, polyvinyl pyrrolidone, polyethylene glycol, cellulose, hydroxyethyl cellulose).

3.14 Composition 3 or any of 3.1 et seq., wherein the sodium chloride and stannous pyrophosphate are made by reacting stannous chloride and tetrasodium pyrophosphate.

3.15 Composition 3 or any of 3.1 et seq., wherein the composition further comprises tetrasodium pyrophosphate (e.g., as an anti-calculus agent, in addition to any tetrasodium pyrophosphate used to make the stannous pyrophosphate), e.g., from 1 to 5% by weight of tetrasodium pyrophosphate, or from 2 to 4%, or 2 to 3% or about 2%.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1: Synthesis of SnPP Using TKPP

Synthesis: 700 g of water is heated to 60° C. in a 1500 mL glass beaker. 105.71 g of tetrasodium pyrophosphate (TSPP) is completely dissolved in the water with a continuous blender stirring at 500 rpm. Then, 144.40 g of $SnCl_2 \cdot 2H_2O$ is added into the solution with stirring, and the reaction mixture is maintained at the same temperature for 30 minutes. A precipitate is observed to begin forming quickly. After 30 minutes, the reaction mixture is cooled down to room temperature. The majority of the supernatant is decanted and removed. The residual material, including the precipitate and remaining supernatant, are transferred into several 50 mL centrifuge tubes. The tubes are centrifuged at a speed of 8500 rpm for 10 minutes to pellet the precipitate, and the supernatant is then removed from each tube. In each tube, the pelleted precipitate is re-suspended with about 5 volumes of water, the suspension is vortexed for one minute, then the tubes are centrifuged again. This washing procedure is repeated two additional times. After removing the last of the supernatant from each tube are put into a dry ice/acetone cooling bath. After the water residues appear to be frozen, the centrifuge tubes are transferred into a freeze dry machine for over 24 hours to remove the last traces of water. The dried samples are used for calculation of reaction yield, FTIR and PXRD characterization and stannous pyrophosphate from Sigma was used as the reference materials.

125.55 grams of stannous pyrophosphate product is collected after freeze-drying, for a yield of 95%. Analysis confirms the identity of the product as stannous pyrophosphate, as described below.

FTIR Experiments:

Infrared spectra are collected using a Bruker Vertex 70 FTIR spectrometer equipped with a GladiATR diamond ATR accessory (Pike technologies, Madison, Wis.). The spectral range is 80-4000 $cm^{-1}$ and a resolution of 4 $cm^{-1}$ is used. All measurements are carried out at room temperature.

Stannous pyrophosphate reference samples are purchased from Sigma. The comparative FTIR spectra are shown in FIG. 1. The data demonstrates that the product obtained matches the spectrum for known stannous pyrophosphate material.

PXRD Experiments:

Powder X-Ray Diffraction (PXRD) of the freeze-dried product is carried out using a Rigaku D/M-2200T automated diffraction system with Cu Kα irradiation ($\lambda$=1.5406 Å). The goniometer is configured in a step-scan mode with 5 s scans during each 0.02° step over a range from $\theta$=5° to $\theta$=50°.

Figure 3:
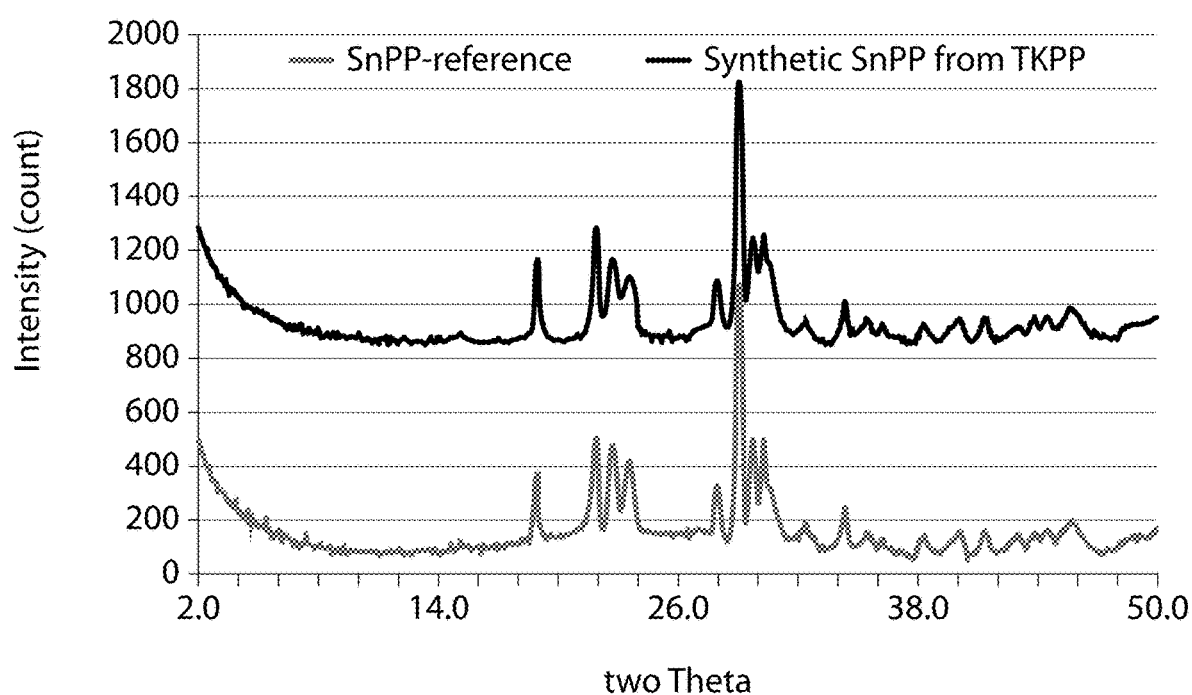
FIG. 3 shows overlaid powder X-ray diffraction (PXRD) spectra comparing the SnPP product made according to the present disclosure, by reacting stannous chloride and tetrapotassium pyrophosphate (TKPP) in water for 30 minutes, followed by precipitation, filtration and freeze-drying (top spectrum) compared to reference SnPP purchased from a global chemical supplier (bottom spectrum).

The same stannous pyrophosphate reference sample as above is used. The results are shown in FIG. 3. No significant difference is found between the two materials, which further confirms the identity of the product as stannous pyrophosphate.

Example 2: Synthesis of SnPP Using DSPP

The synthetic procedure of Example 1 is repeated using 700 g water, 88.78 g of disodium pyrophosphate, and 180.50 g of stannous chloride dihydrate, and a reaction time of 30 minutes. The synthetic method is otherwise as described in Example 1. The product is obtained in a yield of 95.4%. The product is analyzed by FTIR and PXRD as described in Example 1.

Figure 2:
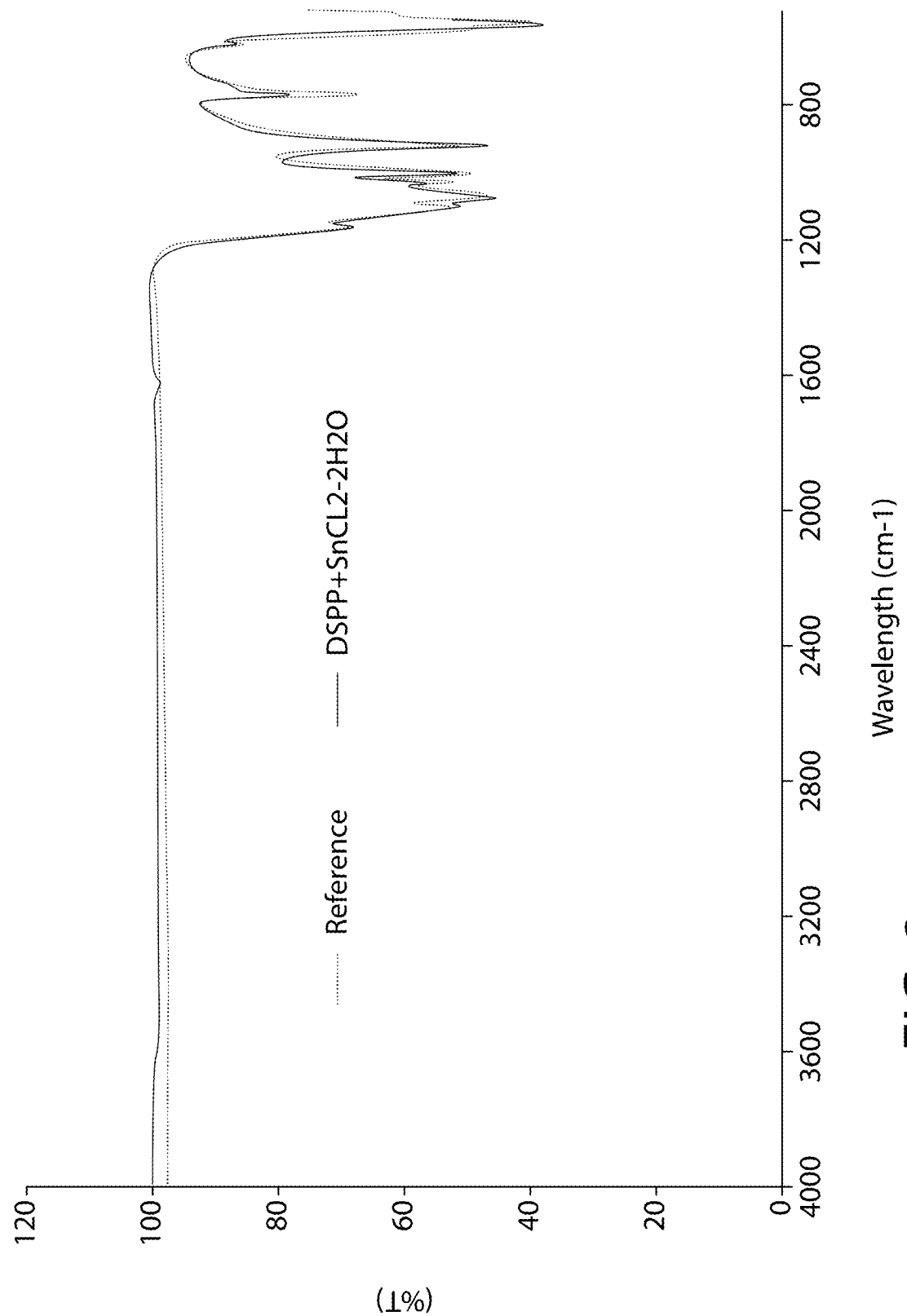
FIG. 2 shows overlaid Fourier-transform infrared (FTIR) spectra comparing the SnPP product made according to the present disclosure, by reacting stannous chloride and disodium pyrophosphate (DSPP) in water for 30 minutes, followed by precipitation, filtration and freeze-drying (spectrum in grey) compared to reference SnPP purchased from a global chemical supplier (spectrum in black).
Figure 4:
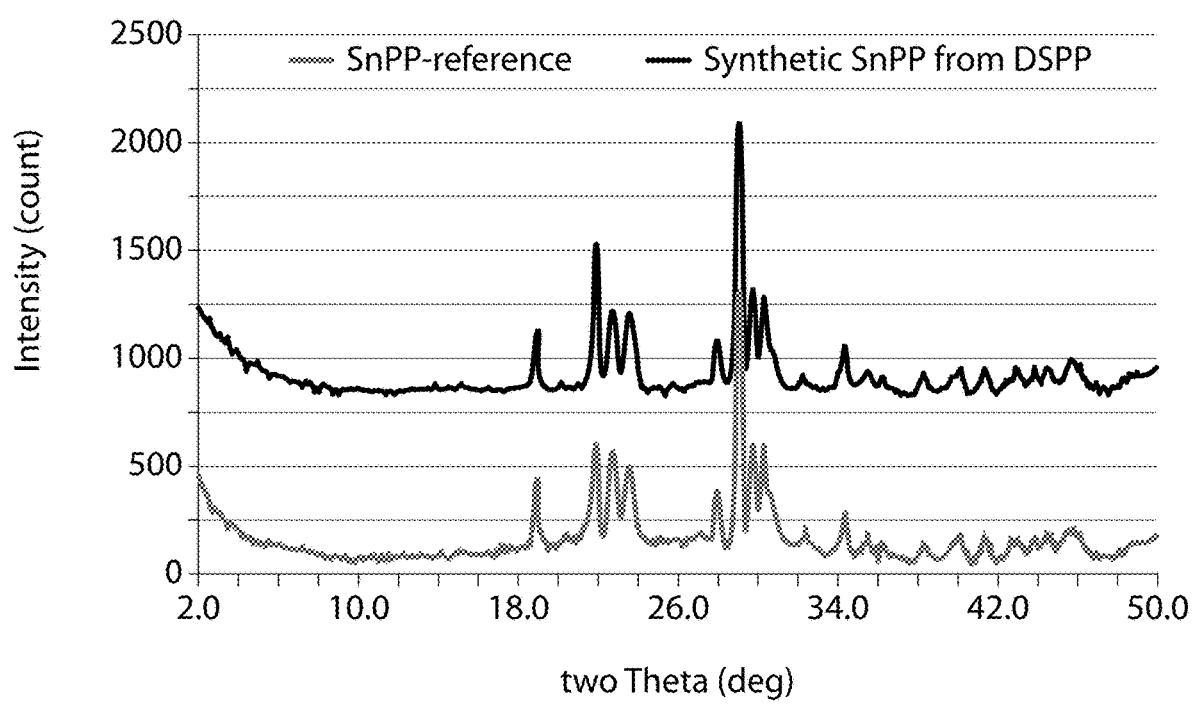
FIG. 4 shows overlaid powder X-ray diffraction (PXRD) spectra comparing the SnPP product made according to the present disclosure, by reacting stannous chloride and disodium pyrophosphate (DSPP) in water for 30 minutes, followed by precipitation, filtration and freeze-drying (top spectrum) compared to reference SnPP purchased from a global chemical supplier (bottom spectrum).

FTIR and PXRD analysis results are similar to that obtained in Example 1 and are consistent with the identity of the product as stannous pyrophosphate. FIG. 2 shows comparative FTIR data, and FIG. 4 shows comparative PXRD data.

Example 3: In-Situ Formation of SnPP in Manufacture of Oral Care Composition

A process development scale plant process is evaluated for the manufacture of a lot of toothpaste. Toothpaste 1 is formulated from the components shown in the table below:

| Ingredient | Wt. % |
| --- | --- |
| Stannous Fluoride | 0.45 |
| Stannous Chloride dihydrate | 1.1% |
| Tetrapotassium pyrophosphate or disodium pyrophosphate | 2-6% |
| Zinc Citrate trihydrate | 0.5% |
| Zinc Oxide | 1.0% |
| Glycerin | 42.4% |
| Propylene Glycol | 4.0% |
| Water (Q.S.) | ~4-8% |
| Polyethylene Glycol 600 | 3.0% |
| Gums, Anionic and Neutral Polymers | 2.85% |
| Methyl vinyl ether/maleic acid copolymer | 0.6% |
| Anionic Surfactant | 1.75% |
| Zwitterionic Surfactant | 1.0% |
| Silicas | 24% |
| Flavors, Colors, Sweeteners | 2.25% |
| Buffer/pH agents | 3.65% |

In a first pre-mix tank A, water (4.5% of final formulation), buffers and sweetener are combined and stirred together. In a second pre-mix tank B, glycerin (7.0% of final formulation) and tetrapotassium or disodium pyrophosphate (1-2.5 wt % of final formulation) are combined and stirred together. In a third pre-mix tank C, glycerin (10% of final formulation), polyethylene glycol, propylene glycol, and gums, anionic and neutral polymers are combined and stirred together. In a fourth pre-mix tank D, water (4.3% of final formulation) is heated to 60° C., and the remaining pyrophosphate salt is added to form a homogenous solution. The stannous chloride dihydrate is then added and the mixture is stirred for 15 minutes at 60° C., then the mixture is cooled to room temperature. A precipitate of stannous pyrophosphate is observed to form. To a primary mixing tank is added the contents of pre-mix Tank C followed by the remaining content of glycerin (25.4% of final formulation), followed by the contents of pre-mix Tank C. The mixing tank is stirred for ten minutes, then is heated to 80° C., and maintained for 30 minutes, then cooled. The contents of pre-mix tank D are then added followed by stirring for 5 minutes. The contents of pre-mix tank B, zinc oxide, zinc citrate, methyl vinyl ether copolymer, and remaining buffer/pH agents are added. After additional mixing, the remaining components of the composition, silicas, colors, flavors, zwitterionic surfactant, and anionic surfactant, are added to yield a gel.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A method of making an oral care composition comprising stannous pyrophosphate, comprising the steps of (1) reacting stannous chloride with a tetrapotassium pyrophosphate, or dipotassium pyrophosphate, in a water or water/alcohol solvent mixture in a reactor tank, (2) precipitating the stannous pyrophosphate product, optionally (3) recovering the stannous pyrophosphate product by filtration, optionally (4) freeze-drying the stannous pyrophosphate product, and (5) transferring the stannous pyrophosphate product into a mixing tank containing at least one oral care ingredient and at least one orally acceptable solvent.

2. The method according to claim 1, wherein the stannous chloride is stannous chloride dihydrate ($SnCl_2$-$2H_2O$).

3. The method according to claim 1, wherein the pyrophosphate is tetrapotassium pyrophosphate.

4. The method according to claim 1, wherein the stannous chloride and the pyrophosphate are combined in a molar ratio of 1:1 to 1:3.

5. The method according to claim 1, wherein solvent for step (1) is water.

6. The method according to claim 1, wherein the solvent for step (1) is a water/alcohol mixture.

7. The method according to claim 6, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.

8. The method according to claim 1, wherein the step (3) and step (4) are omitted, and step (2) yields a liquid slurry of the stannous pyrophosphate product precipitate in the water or water/alcohol solvent mixture and this slurry is transferred into the mixing tank of step (5).

9. The method according to claim 1, wherein step (4) is omitted, and the filtered solid from step (3) is transferred into the mixing tank of step (5).

10. The method according to claim 1, wherein the reaction step (1) is substantially complete in 0-3 hours.

11. The method according to claim 1, wherein the method further comprises the step of incorporating stannous fluoride into the oral care composition.

12. A method of making stannous pyrophosphate, comprising the steps of (1) reacting stannous chloride with tetrapotassium pyrophosphate, dipotassium pyrophosphate, or disodium pyrophosphate in a water or water/alcohol solvent mixture, (2) precipitating the stannous pyrophosphate product, (3) recovering the stannous pyrophosphate product by filtration, and (4) freeze-drying the stannous pyrophosphate product.

13. The method of claim 12, wherein the stannous chloride is stannous chloride dihydrate ($SnCl_2$-$2H_2O$).

14. The method of claim 12, wherein the pyrophosphate salt is dipotassium pyrophosphate, or tetrapotassium pyrophosphate.

15. The method according to claim 12, wherein the stannous chloride and the di-or tetra-alkali pyrophosphate are combined in a molar ratio of 1:1 to 1:3.

16. The method according to claim 12, wherein solvent for step (1) is water.

17. The method according to claim 12, wherein the solvent for step (1) is a water/alcohol mixture.

18. The method according to claim 17, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.

19. An oral care composition comprising stannous pyrophosphate made according to the method of claim 12.

20. An oral care composition comprising (a) stannous pyrophosphate and sodium chloride in a molar ratio of about 2 parts sodium chloride to one part stannous pyrophosphate, (b) stannous pyrophosphate and potassium chloride in a molar ratio of about 2 parts potassium chloride to one part stannous pyrophosphate, or (c) stannous pyrophosphate and potassium chloride in a molar ratio of about 4 parts potassium chloride to one part stannous pyrophosphate.

* * * * *